US009974817B2

(12) United States Patent
Kullisaar et al.

(10) Patent No.: US 9,974,817 B2
(45) Date of Patent: May 22, 2018

(54) METHOD OF TREATMENT USING LACTOBACILLUS FERMENTUM ME-3

(71) Applicant: University of Tartu, Tartu (EE)

(72) Inventors: Tiiu Kullisaar, Tartu (EE); Mihkel Zilmer, Tartu (EE); Imbi Smidt, Tartu (EE); Kersti Zilmer, Tartu (EE); Marika Mikelsaar, Tartu (EE); Pirje Hütt, Tartu (EE)

(73) Assignee: UNIVERSITY OF TARTU, Tartu (EE)

( * ) Notice: Subject to any disclaimer, the term of this patent is extended or adjusted under 35 U.S.C. 154(b) by 147 days.

(21) Appl. No.: 14/655,328

(22) PCT Filed: Dec. 20, 2013

(86) PCT No.: PCT/IB2013/061216
§ 371 (c)(1),
(2) Date: Jun. 24, 2015

(87) PCT Pub. No.: WO2014/102692
PCT Pub. Date: Jul. 3, 2014

(65) Prior Publication Data
US 2015/0343003 A1 Dec. 3, 2015

(30) Foreign Application Priority Data
Dec. 24, 2012 (GB) .................................. 1223370.6

(51) Int. Cl.
*A61K 9/48* (2006.01)
*A61K 35/747* (2015.01)
*A23G 1/42* (2006.01)

(52) U.S. Cl.
CPC ............ *A61K 35/747* (2013.01); *A23G 1/423* (2013.01); *A61K 9/48* (2013.01); *A61K 9/4891* (2013.01); *A23Y 2220/35* (2013.01)

(58) Field of Classification Search
None
See application file for complete search history.

(56) References Cited

U.S. PATENT DOCUMENTS

| | | | |
|---|---|---|---|
| 5,753,703 A | 5/1998 | Cavazza et al. | |
| 7,244,424 B2 * | 7/2007 | Mikelsaar | A61K 35/747 424/93.1 |
| 2004/0071680 A1 | 4/2004 | Song et al. | |
| 2004/0126356 A1 | 7/2004 | Pang et al. | |
| 2004/0151708 A1 | 8/2004 | Mikelsaar et al. | |

FOREIGN PATENT DOCUMENTS

| | | |
|---|---|---|
| EP | 2262514 | 12/2010 |
| JP | H09176005 A | 7/1997 |
| WO | 03002131 | 1/2003 |
| WO | 2009110646 | 9/2009 |

OTHER PUBLICATIONS

Kullisaar et al. (Nutrition J., 15:93, 1-6, 2016).*
International Application No. PCT/IB2013/061216, International Search Report and Written Opinion, dated Feb. 27, 2014, 10 pages.
Marika Mikelsaar et al., "Lactobacillus fermentum ME-3—an antimicrobial and antioxidative probiotic", *Microbial Ecology in Health and Disease*, vol. 101, No. 10, Jan. 1, 2009 (Jan. 1, 2009), pp. 1-27.
Tiiu Kullisaar et al., "An antioxidant probiotic reduces postprandial lipemia and oxidative stress", *Central European Journal of Biology*, vol. 6, No. 1, Nov. 13, 2010 (Nov. 13, 2010), pp. 32-40.
Arribas et al., "Evaluation of the preventative effects exerted by Lactobacillus fermentum in an experimental model of septic shock induced in mice", British Journal of Nutrition, vol. 101, 2009, pp. 51-58.
Kullisaar et al., "Antioxidative probiotic fermented goats' milk decreases oxidative stress-mediated atherogenicity in human subjects", British Journal of Nutrition, vol. 90, 2003, pp. 449-456.
Mane et al., "Lactobacillus fermentum CECT 5716 prevents and reverts intestinal damage on TNBS-induced colitis in mice", Inflamm Bowel Dis, vol. 15, No. 8, Aug. 2009, pp. 1155-1163.
Mikelsaar et al., "Regulation of plasma lipid profile by lactobacillus fermentum (probiotic strain ME-3 DSM14241) in a randomised controlled trial of clinically healthy adults", BMC Nutrition, vol. 1:27, Oct. 19, 2015, pp. 1-11.
Peran et al., "Lactobacillus fermentum, a probiotic capable to release glutathione, prevents colonic inflammation in the TNBS model of rat colitis", Int J Colorectal. Dis., vol. 21, Issue 8, Dec. 2006, pp. 737-746.
Songisepp et al., "Evaluation of the functional efficacy of an antioxidative probiotic in healthy volunteers", Nutrition Journal, vol. 4:22, Aug. 4, 2005, pp. 1-10.
West et al., "Lactobacillus fermentum (PCC®) supplementation and gastrointestinal and respiratory-tract illness symptoms: a randomised control trial in athletes", Nutrition Journal, vol. 10:30, Apr. 11, 2011, pp. 1-11.
Becker et al., "Simvastatin vs Therapeutic Lifestyle Changes and Supplements: Randomized Primary Prevention Trial," Mayo Clinic Proc., Jul. 2008, 83(7) 758-764.
Amanullah et al., "Association of hs-CRP with Diabetic and Non-Diabetic Individuals," Jordan Journal of Biological Sciences, vol. 3, No. 1, Jan. 2010, pp. 7-12.
Pepys et al., "C-reactive protein: a critical update," J. Clin. Invent., 111:1805-1812 (2003).

* cited by examiner

*Primary Examiner* — Brian Gangle
(74) *Attorney, Agent, or Firm* — Kilpatrick Townsend & Stockton LLP

(57) ABSTRACT

The invention provides a composition comprising *Lactobacillus fermentum* ME-3 strain DSM 14241 for use in preventing, alleviating the symptoms of or treating, alone or as an adjuvant component, a metabolic syndrome related disorder selected from prediabetes, type 2 diabetes and cardiovascular disease. The effect may be achieved by simultaneously: decreasing the level of glycated haemoglobin HbA1c, decreasing or preventing low-grade inflammation on a cellular level and increasing the level of adiponectin.

11 Claims, 2 Drawing Sheets

|  | Start | 24 hours | 48 hours | 1 week | 2 weeks | 3 weeks |
|---|---|---|---|---|---|---|
| A (30% cacao) | 7.90 | 7.90 | 7.70 | 8.20 | 8.10 | 7.40 |
| B (56% cacao) | 8.10 | 8.30 | 7.90 | 8.30 | 8.30 | 7.30 |
| C (70% cacao) | 7.60 | 7.80 | 7.40 | 6.90 | 7.50 | 7.00 |
| D (85% cacao) | 7.90 | 7.30 | 7.20 | 6.70 | 7.20 | 6.40 |

METHOD OF TREATMENT USING *LACTOBACILLUS FERMENTUM* ME-3

The present invention is in the fields of medicine and nutrition, particularly preventing, alleviating the symptoms of, treating and/or providing adjuvant treatment, e.g. as an adjuvant component, for inflammatory diseases such as cardiovascular disease, stroke, and metabolic syndrome. The invention relates to compositions comprising *Lactobacillus fermentum* ME-3 for use in preventing, alleviating the symptoms of, treating and/or providing adjuvant treatment for inflammatory diseases and methods of preventing, alleviating the symptoms of, treating and/or providing adjuvant treatment for inflammatory diseases using compositions comprising *Lactobacillus fermentum* ME-3. Preferred such diseases are metabolic syndrome related conditions (preferably selected from pre-diabetes, diabetes, cardiovascular disease). This effect of compositions comprising *Lactobacillus fermentum* ME-3 may be achieved by reduction of the level of glycated haemoglobin (HbA1c), increasing the level of adiponectin, and/or decreasing the level of low-grade cellular inflammation (reduction of the level of high sensitive C-reactive protein and interleukin 6, and increasing the level of interleukin 10).

BACKGROUND OF THE INVENTION

Probiotic organisms are live microorganisms that are beneficial to the host organism. Many species and strains of probiotic bacteria are known in the art. Lactic acid bacteria (LAB) and bifidobacteria are the most common types of microbes used as probiotics but certain yeasts and bacilli may also be used. Probiotics are commonly consumed as part of fermented foods with specially added active live cultures, such as in yogurt, soy yogurt, or as dietary supplements.

*Lactobacillus fermentum* ME-3 strain DSM 14241 has been described previously as an antioxidative probiotic (EP1401457). Many other species and strains of probiotic bacteria are known in the art. However, there are few studies where the effects of different probiotic bacteria have been compared within the same clinical setting. In vivo probiotic bacteria differ in their ability to induce clinically relevant changes in subjects. Some effects are strain-specific. Some bacteria have been disclosed that may possess a weak anti-inflammatory effect reflected as a decrease in serum hsCRP levels in healthy adults (Kekkonen et al., World J Gastroenterol. 2008; 14(13):2029-36). In general, only preliminary evidence exists for the health claims stated for any probiotic bacteria (Mikelsaar & Zilmer (2009) Microbial Ecology in Health and Disease, 21: 1-27). A few of the strains currently marketed have been sufficiently developed in basic and clinical research to warrant application for health claim status to a regulatory agency such as the Food and Drug Administration or European Food Safety Authority.

Thus, there remains a pressing need to identify new strains of probiotic bacteria that can be used in a clinical setting, and to prevent, alleviate the symptoms of, treat and provide adjuvant treatment e.g. as an adjuvant component for inflammatory diseases. Preferred such diseases are metabolic syndrome related conditions (preferably selected from pre-diabetes, diabetes, cardiovascular disease).

SUMMARY OF THE INVENTION

The present inventors have found that *Lactobacillus fermentum* ME-3, unlike other *Lactobacillus* sp. (Mikelsaar & Zilmer (2009) Microbial Ecology in Health and Disease, 21: 1-27), is a significant inhibitor of pro-inflammatory markers, such as glycated haemoglobin HbA1c, high sensitivity C-reactive protein (hsCRP) and IL-6, and is also capable of stimulating production of the anti-inflammatory and anti-diabetic peptide adiponectin. Consequently, as a result of identifying the underlying mechanism by which the probiotic strain *Lactobacillus fermentum* ME-3 acts, the present inventors have found that it can be used to prevent, alleviate the symptoms of, treat and/or be used as an adjuvant treatment e.g. as an adjuvant component for inflammatory diseases and in particular metabolic syndrome related conditions (preferably selected from pre-diabetes, diabetes, cardiovascular disease). This is particularly surprising, as *Lactobacillus fermentum* ME-3 has previously been reported as an antimicrobial and antioxidative probiotic (EP1401457 & Mikelsaar & Zilmer (2009) Microbial Ecology in Health and Disease, 21: 1-27).

The invention therefore provides a composition comprising *Lactobacillus fermentum* ME-3, particularly *Lactobacillus fermentum* ME-3 strain DSM 14241 deposited at the Deutsche Sammlung für Mikroorganismen und Zelkulturen GmbH-s on 19 Apr. 2001, for use in preventing, alleviating the symptoms of, treating and/or providing adjuvant treatment, e.g. as an adjuvant component, for an inflammatory disease and in particular metabolic syndrome related conditions. The invention also provides a method of preventing, alleviating the symptoms of, treating and/or providing adjuvant treatment, e.g. as an adjuvant component, for an inflammatory disease, and in particular metabolic syndrome related conditions in a subject comprising administering an effective amount of a composition comprising *Lactobacillum fermentum* ME-3 strain DSM 14241 to said subject. The invention further provides the use of *Lactobacillum fermentum* ME-3 strain DSM 14241 in the manufacture of a medicament and/or an adjuvant medicament for the prevention, alleviation of the symptoms, treatment and/or adjuvant treatment, e.g. for an inflammatory disease and in particular metabolic syndrome related conditions.

Because of its mechanism of action, *Lactobacillus fermentum* ME-3 is particularly useful in certain subject subpopulations such as asymptomatic subjects, including those with low-grade inflammation, at risk of developing an inflammatory disease, such as cardiovascular disease (CVD), type 2 diabetes or metabolic syndrome; and patients who have suffered a stroke. The present inventors have also discovered that *Lactobacillus fermentum* ME-3 is also particularly beneficial when used in combination with one or more vitamins and/or monocalin K.

The present invention therefore provides a composition comprising *Lactobacillus fermentum* ME-3, for use in preventing, alleviating the symptoms of, treating and/or providing adjuvant treatment (e.g. as an adjuvant component), for an inflammatory disease and in particular for metabolic syndrome related conditions by one or more of:
  a. decreasing the level of glycated haemoglobin HbA1c;
  b. decreasing or preventing low-grade inflammation on a cellular level; and
  c. increasing the level of adiponectin,
in a subject.

The invention also provides a method of preventing, alleviating the symptoms of, treating and/or providing adjuvant treatment (e.g. as an adjuvant component), for an inflammatory disease and in particular for metabolic syndrome related conditions in a subject by one or more of:

a. decreasing the level of glycated haemoglobin HbA1c;
b. decreasing or preventing low-grade inflammation on a cellular level; and
c. increasing the level of adiponectin, comprising administering an effective amount of a composition comprising *Lactobacillum fermentum* ME-3 strain DSM 14241 to said subject.

The invention also provides *Lactobacillus fermentum* ME-3 strain DSM 14241 for use in the manufacture of a medicament and/or an adjuvant medicament for the prevention, alleviation of the symptoms, treatment and/or adjuvant treatment (e.g. as an adjuvant component), for an inflammatory disease and in particular for metabolic syndrome related conditions by one or more of:
a. decreasing the level of glycated haemoglobin HbA1c;
b. decreasing or preventing low-grade inflammation on a cellular level; and
c. increasing the level of adiponectin
in a subject.

In all cases, as a result of the treatment with *Lactobacillus fermentum* ME-3 strain DSM 14241, preferably at least two and preferably all of:
a. decreasing the level of glycated haemoglobin HbA1c;
b. decreasing or preventing low-grade inflammation on a cellular level; and
c. increasing the level of adiponectin
occurs. Preferably these occur simultaneously.

For example treatment with *Lactobacillus fermentum* ME-3 strain DSM 14241 may result in decreasing the level of glycated haemoglobin HbA1c and decreasing or preventing low-grade inflammation on a cellular level; decreasing the level of glycated haemoglobin HbA1c and increasing the level of adiponectin; or decreasing or preventing low-grade inflammation on a cellular level and increasing the level of adiponectin. Preferably these occur simultaneously.

Glycated Haemoglobin HbA1c

Inflammation, chronic low-grade inflammation and non-specific haemoglobin (Hb) glycation are some of the most important risk factors of pre-diabetes, diabetes and cardiovascular diseases. In general, the reference range, found in healthy subjects, is about 20-40 mmol/mol (4%-5.9% glycated haemoglobin) ("Hemoglobin A1c Test". MedicineNet.com). Abnormal Hb glycation, which can be defined as a level of glycated haemoglobin greater than or equal to about 48 mmol/mol (or ≥6.5% glycated haemoglobin) (Kekkonen R A, et al. World J Gastroenterol. 2008; 14(13):2029-36) is linked to the physiology of aging and specifically to the pathophysiology of type 2 diabetes. Therefore, any abnormal haemoglobin glycation, i.e glycation in excess of about 40 mmol/mol (or ≥5.9% haemoglobin), can enhance the development of CVD.

According to guidelines (ADA Diabetes Care, 2011, etc) for people without diabetes, the normal range for HbA1c is between 4% and 5.6%, HbA1c levels between 5.7% and 6.4% (prediabetic status) indicate an increased risk of type two diabetes, and levels of 6.5% or higher indicate diabetes. For example, people within an HbA1c range of 5.5-6.0% have a 5-year cumulative incidence of diabetes that ranges from 12 to 25% (ADA Diabetes Care, 2011). Therefore, any lowering of the level of HbA1c is accepted as a principal target for the prevention, alleviation and treatment of pre-diabetes and diabetes.

In the target population, the level of glycated haemoglobin is greater than or equal to about 40 mmol/mol, for example greater than or equal to about 48, 50, 53, 55, 60 or 65 mmol/mol. This can also be expressed as about 5.9%, 6.5%, 7.0%, 7.2%, 7.6% or 8.1% glycated haemoglobin.

Alternatively defined the target population may have HbA1c levels that are indicative of prediabetic status (ADA Diabetes Care, 2011), i.e. HbA1c levels between 5.7% and 6.4% or levels that indicate diabetes (ADA Diabetes Care, 2011), i.e. HbA1c levels of 6.5% or higher.

Levels of non-specific haemoglobin (Hb) glycation (i.e. the levels of level of glycated haemoglobin HbA1c) may be measured as described herein or by any method known in the art. For example, levels of non-specific haemoglobin (Hb) glycation (i.e. the levels of level of glycated haemoglobin HbA1c) may be measured as described in references (Pitsavos et al., Rev Diabet Stud. 2007; 4(2):98-104) and (Festa & Haffner. Circulation. 2005; 17; 111 (19):2414-5.)

Adiponectin

Adiponectin is an adipokine polypeptide hormone produced exclusively by adipocytes. Among the adipokines, adiponectin is the most abundant. Adiponectin modulates a number of metabolic processes, including glucose regulation and fatty acid oxidation and is typically present in the blood at a level of about 5 to 21 ng/ml in healthy individuals. Levels of adiponectin are reduced in the target subject population, and are typically less than about 10-20 ng/ml, or less than about 20 ng/ml, 15 ng/ml, 10 ng/ml, 8 ng/ml, 5 ng/ml or even lower.

Adiponectin levels can be measured as described herein or by any method known in the art. For example, levels of adiponectin may be measured as described in reference (Ebinuma H, et al. Clin Chem. 2007 August; 53(8):1541-4. Epub 2007 Jun. 28.)

Low-Grade Inflammation on a Cellular Level

Low-grade inflammation (LGI) occurs typically in vasculature and adipose tissue of a subject. LGI is typically chronic in its nature. Well-accepted markers of low-grade inflammation on cellular level include high sensitivity C-reactive protein (hsCRP) and IL-6.

CRP is an acute-phase reactant that belongs to highly conserved pentraxin family of plasma proteins. CRP is produced mainly in the liver but also in the kidney, neurons, alveolar macrophages and atherosclerotic lesions (Devaraj S et al. Arterioscler Thromb Vasc Biol. 2008; 28: 1368-1374). hsCRP is also an excellent marker of low-grade (high-normal) inflammation at the cellular level. It has been shown that CRP binds to the apoptotic cells and so it may be a tier of innate immunity against the pathogenic expression of the apoptotic cells and that way increases in response to noxious stimuli that inevitably induce cellular and/or tissue injury (Chang M K et al. PNAS USA. 2002 Oct. 1; 99(20):13043-13048). Many studies have shown that hsCRP stimulates monocytes to produce pro-inflammatory factors, including IL-6. hsCRP also activates the complement system and induces vascular endothelial cellular dysfunction and the migration and proliferation of vascular smooth muscle cells (Li J T et al., Scand J Immunol. 2007; 66 (5):555-62).

As used herein, the term "low-grade inflammation on cellular level" refers to an inflammatory status wherein the C-reactive protein (CRP) level in blood serum of a subject is less than or equal to 20.0 mg/l (Van den Bruel A et al. (2011) BMJ. 2011 Jun. 8; 342:d3082), specifically from about 3.0 to 10.0 mg/l. The lowest cardiovascular risk, has been seen in patients who had both an hsCRP<1 mg/L and LDL-C<70 mg/dL (Koenig W. 2013. Int J Cardiol, 168, 5126-5134). The American Heart Association and the Centers for Disease Control and Prevention recommended the following interpretation of hsCRP results: <1 mg/L—low risk; 1-3 mg/L—average risk; >3 mg/L—high risk (Pearson T A, et al. 2003. Circulation, 107:499-511). In particular embodiments, the target subject group has a CRP level of less than or equal to 10.0 mg/l, from about 3.0 to 10.0 mg/l, from about 4.0 to 9.0 mg/l, or from about 5.0 to 8.0 mg/l.

Levels of CPR and hsCRP may be measured as described herein or by any method known in the art. For example, levels of CRP and hsCRP may be measured as described in Pearson T A et al. cited above, and the levels are preferably measured in this way.

As described herein, low-grade inflammation on cellular level is linked to inflammatory diseases.

IL-6 is widely accepted as a central and crucial pro-inflammatory marker (Lu X T et al. 2013. J Cardiovasc Pharmacol. 2013 July; 62(1):6-12). It is the major cellular factor that regulates hsCRP synthesis in hepatocytes. IL-6 is produced in a variety of tissues, including activated leukocytes, adipocytes, and endothelial cells. IL-6 reference values are typically less than 3.3 ng/ml in blood serum of clinically healthy persons (endemic reference value).

In particular embodiments, the target subject group has an IL-6 level of greater than about 3.3 ng/ml. Specifically, the target subject group may have an IL-6 level of about 3.3 to 10.0 ng/ml, about 4.0 to 8.0 ng/ml, or about 5.0 to 7.0 ng/ml.

Levels of IL-6 may be measured as described herein or by any method known in the art. For example, levels of IL-6 may be measured as described in (Nordan, R. P. et al. 2001. Current Protocols in Immunology. 17:6.6.1-6.6.5.)

IL-10 is well accepted as anti-inflammatory marker (Tsai T T et al. 2013, J Biomed Sci. 2013 Jun. 25; 20:40) Some authors have reviewed association between high-normal (low-grade) systemic inflammation and type 2 diabetes including a greater risk developing CVD (Pitsavos et al., Rev Diabet Stud. 2007; 4(2):98-104) and (Festa & Haffner Circulation. 2005; 17; 111 (19):2414-5.)

Levels of IL-10 may be measured as described herein or by any method known in the art. For example, levels of IL-10 may be measured as described in Tsai T T et al. cited above.

Inflammatory Diseases

Due to the underlying mechanism by which *Lactobacillus fermentum* ME-3 alters the profile of pro- and anti-inflammatory markers, the present inventors have found that the probiotic bacterial strain is useful for preventing, alleviating the symptoms of, treating and/or providing adjuvant treatment, for an inflammatory disease and in particular metabolic syndrome related conditions. In particular, the present invention can be used to prevent, alleviate the symptoms of, treat and/or be an adjuvant treatment for an inflammatory disease, wherein said inflammatory disease or disorder is a CVD, a neurodegenerative disease, Alzheimer's disease, atherosclerosis, cancer, stroke, a metabolic disorder, metabolic syndrome, pre-diabetes or type 2 diabetes.

Inflammation and non-specific haemoglobin (Hb) glycation are one of the most important risk factors of the inflammatory diseases type 2 diabetes and CVD. Abnormal Hb glycation is linked to physiology of aging and especially to pathophysiology of type 2 diabetes. Therefore permanent low-grade (or high-normal) inflammation (e.g. CRP level of about 3.0 to about 10.0 mg/l) and advanced glycation of haemoglobin (e.g. glycation above 40 mmol/mol or 5.9%) both can enhance the development of cardiovascular diseases. Some authors have reviewed association between high-normal (low-grade) systemic inflammation and type 2 diabetes including the greater risk developing cardiovascular disease (CVD) (Pitsavos et al., Rev Diabet Stud. 2007; 4(2):98-104, Festa & Haffner Circulation. 2005; 17; 111 (19):2414-5).

Thus, by identifying that *Lactobacillus fermentum* ME-3 had a profound suppressive effect on pro-inflammatory markers by decreasing the level of glycated haemoglobin HbA1c and decreasing or preventing low-grade inflammation on a cellular level, the inventors have identified a target population of subjects at risk of developing CVD and type 2 diabetes who would benefit from *Lactobacillus fermentum* ME-3.

Elevated levels of high sensitive C-reactive protein (hsCRP) as well as IL-6 (interleukine-6) and TNF-α (tumour necrosis factor-α) have also been accepted as strong markers related to CVD risk, mainly in type 2 diabetes subjects but also non-diabetic persons. Therefore, the present inventors focussed on hsCRP as a marker of chronic, subclinical LGI related to CVD. The American Heart Association and the Centers for Disease Control and Prevention recommended the following interpretation of hsCRP results: <1 mg/L—low risk; 1-3 mg/L—average risk; >3 mg/L—high risk (Pearson T A et al. cited above). Low-grade (high-normal) inflammation on the cellular level may occur in apparently healthy individuals, placing them at increased cardiovascular disease and neurodegenerative disease risk during ageing and/or advanced Hb glycation (Rifai & Ridker Clin Chem. 200349(4):666-9).

Thus, the present inventors have found that a particular target population for prophylactic treatment and/or prophylactic adjuvant treatment (e.g. as an adjuvant component with *Lactobacillus fermentum* ME-3 are subjects that appear to be healthy, or are currently asymptomatic for an inflammatory disease and/or metabolic syndrome related conditions. In a particular embodiment, the target population is asymptomatic for CVD, a neurodegenerative disease, Alzheimer's disease, atherosclerosis, cancer, stroke, a metabolic disorder, metabolic syndrome, or type 2 diabetes. In a further embodiment, the target population may be asymptomatic for CVD and/or type 2 diabetes.

By "asymptomatic" it is meant that the subject provides no evidence (e.g. outward evidence) of the existence of the particular disease such as an inflammatory disease and/or metabolic syndrome related conditions. In particular, the subject may provide no evidence of the existence of CVD, a neurodegenerative disease, Alzheimer's disease, atherosclerosis, cancer, stroke, a metabolic disorder, metabolic syndrome, or type 2 diabetes. In a further embodiment, the subject may provide no evidence of the existence of CVD, and/or type 2 diabetes. However, the subject may be at risk of developing the inflammatory disease(s) and/or metabolic syndrome related conditions in the future or may be at any stage of developing or having the inflammatory disease(s) and/or metabolic syndrome related conditions but not yet showing any detectable, obvious and/or overt symptoms, i.e. may be prediabetic (this being the state in which some but not all of the diagnostic criteria for diabetes are met, but which is itself asymptomatic). A subject with prediabetes is at risk of developing type 2 diabetes. The progression into diabetes mellitus from prediabetes is approximately 25% over three to five years (Nathan et al. (2007). Diabetes Care 30 (3): 753-9).

In some embodiments, the subject may be suffering from one inflammatory disease, but be asymptomatic for a second or further inflammatory disease. In other embodiments, the subject may be suffering from more than one, e.g. 2, 3, 4, 5, 6, 7 or more, inflammatory diseases and yet still be asymptomatic for one or more, e.g. 1, 2, 3, 4, 5, 6, 7 or more, further inflammatory diseases. In a specific example, the subject may be asymptomatic for CVD and/or type 2 diabetes, but may be suffering from metabolic syndrome. In an alternative embodiment, the subject may be suffering from cancer, but still be asymptomatic for one or more of CVD, a neurodegenerative disease, Alzheimer's disease, atherosclerosis, stroke, a metabolic disorder, metabolic syndrome, and/or type 2 diabetes.

In one embodiment, the asymptomatic subject has a CRP level of ≤20 mg/l. Specifically, the asymptomatic subject may have a CRP level from about 3.0 to 10.0 mg/l, from about 4.0 to 9.0 mg/l, or from about 5.0 to 8.0 mg/l.

In some embodiments, the asymptomatic subject has a glycated haemoglobin level that is greater than or equal to about 40 mmol/mol. Specifically, the asymptomatic subject may have a glycated haemoglobin level greater than or equal to about 48, 50, 53, 55, 60 or 65 mmol/mol.

In some embodiments, the asymptomatic subject has an IL-6 level of greater than about 3.3 ng/ml. Specifically, the asymptomatic subject may have an IL-6 level of about 3.3 to 10.0 ng/ml, about 4.0 to 8.0 ng/ml, or about 5.0 to 7.0 ng/ml.

In some embodiments, the asymptomatic subject has an adiponectin level of less than about 10-20 ng/ml. Specifically, the asymptomatic subject may have an adiponectin level less than about 20 ng/ml, 15 ng/ml, 10 ng/ml, 8 ng/ml, 5 ng/ml or even lower.

The present invention is particularly useful in the treatment of subjects with metabolic syndrome, and in particular as an adjuvant, (e.g. as an adjuvant component), in the treatment of subjects with metabolic syndrome, who may be regarded as asymptomatic for type 2 diabetes and CVD but at risk of developing these, and possibly other, inflammatory diseases (i.e. prediabetic subjects).

Treatment, prevention, adjuvant treatment and/or alleviation of the symptoms of metabolic syndrome according to the invention may prevent the development of inflammatory diseases such as CVD and type 2 diabetes. Metabolic syndrome (MS) is a cluster of metabolic abnormalities (Juturu & Gormley 2005 Current Nutrition & Food Science, 1(1), 1-11.; Herder, et al. Journal of Clinical Endocrinology & Metabolism 92.12 (2007): 4569-4574, Kadowaki, Takashi, et al. Journal of Clinical Investigation 116.7 (2006): 1784-1792, Oliveira, A., et al. Nutrition, Metabolism and Cardiovascular Diseases 21.5 (2011): 347-354.) such as abdominal obesity, atherogenic dyslipidaemia, elevated blood pressure, insulin resistance, glucose intolerance, prediabetes, type 2 diabetes and thus, ultimately can lead to CVD.

Metabolic syndrome can thus be described as an example of an inflammatory disease as broadly defined herein. Metabolic syndrome related disorders include disorders or diseases that are found in patients or subjects with metabolic syndrome and/or which may arise as a direct or indirect consequence of metabolic syndrome. Specific examples are prediabetes, type 2 diabetes and CVD.

Thus, the present inventors have found that a particular target population for prophylactic treatment with a compositions containing *Lactobacillus fermentum* ME-3 are also subjects that appear to be clinically healthy, or are currently clinically healthy for metabolic syndrome, and for metabolic syndrome related conditions.

As well as the pro-inflammatory markers mentioned above, it has been suggested that adiponectin plays an important role in the development of type 2 diabetes and is associated with pathological events by sensitizing insulin and improving lipid metabolism. Low adiponectin levels have been reported to be closely associated with hyperinsulinaemia, type 2 diabetes, obesity, metabolic syndrome, atherosclerosis, and dyslipidaemia (Kadowaki et al. Endocr Rev. 2005; 26(3):439-51). Several epidemiological studies suggest that high adiponectin appears to be protective against the development of type 2 diabetes, cardiovascular diseases and atherosclerosis (Knobler et al. Eur J Endocrinol. 2006; 154(1):87-92, Spranger et al. Lancet. 2003; 361(9353):226-8). In addition, it has been reported that adiponectin has an anti-inflammatory effect and that its concentration is associated negatively with the degree of inflammatory markers, such as hsCRP, IL-6, and TNF-α (Puglisi & Fernandez J Nutr. 2008 December; 138(12): 2293-6. Review). The present invention is therefore particularly effective in the prevention, alleviation of the symptoms, treatment and/or adjuvant treatment of type 2 diabetes, as the present inventors have shown that *Lactobacillus fermentum* ME-3 can simultaneously reduce the level of markers such as hsCRP, IL-6, HbA1c, as well insulin resistance (TG/HDL-Chol) and increase the level of adiponectin and IL-10.

Adiponectin levels are generally lower in type 2 diabetic subjects than in nondiabetic subjects Nayak, et al. Arch Physiol Biochem. 2009; 115(1):28-33. Additionally, previous cell culture studies have shown that adiponectin can suppress CRP synthesis and secretion from aortic endothelial cells and hepatocytes. On the other hand CRP can also suppress adiponectin expression and secretion from adipocytes (Devaraj et al. Arterioscler Thromb Vasc Biol. 2008; 28: 1368-1374). The interaction of these two markers of inflammatory diseases thus makes *Lactobacillus fermentum* ME-3 particularly effective in preventing, alleviating the symptoms of, treating and/or use as an adjuvant in treating the diseases listed herein, as *Lactobacillus fermentum* ME-3 simultaneously alters the level of markers such as hsCRP and IL-6, and increase the level of adiponectin.

Chronic low-grade (high-normal) inflammation on the cellular level is now believed to be a significant cause of many age-related disorders including Alzheimer's disease, cancer, cardiovascular disease, type 2 diabetes, and frailty in the elderly. Atherosclerosis may be a major driver of other age-related disorders, as damaged vascular endothelium activates inflammatory processes by up-regulation cytokines like IL-6 and hsCRP. Chronic systemic inflammation then disturbs many other organ systems leading to other age-related disorders. Low level increases in hsCRP have been reported in various conditions and diseases states that are thought to be associated with inflammation, and in the case of CVD hsCRP has been reported to predict cardiovascular outcomes independently of other conventional risk markers (Verma et al. Nat. Clin. Pract. Cardiovasc Med. 2005; 2(1):29-36, Ridker P M. Circulation. 2003; 28; 107(3):363-9).

The present invention therefore also encompasses preventing, alleviating the symptoms of, treating and/or providing adjuvant treatment for Alzheimer's disease, cancer and atherosclerosis.

The inventors have also found that *Lactobacillus fermentum* ME-3 can be used as an adjuvant treatment, for example as component in complex treatment, for patients that have suffered a stroke. In one embodiment, the *Lactobacillus fermentum* ME-3 can be used as an adjuvant treatment during in the period of hospitalisation for patients recovering from a stroke. When a patient has suffered a stroke, if there is evidence of a high level of inflammation, i.e. any inflammatory marker being above the cut-off level disclosed herein, then antibiotics may be administered to that patient. As described in Example 2 herein, a composition comprising *Lactobacillus fermentum* ME-3 was able to significantly reduce the level of hsCRP in subjects who had suffered a stroke, and therefore reduce the need for administration of antibiotics to stroke patients. This has the benefit of reducing the occurrence of side effects from antibiotics in stroke patients during recovery periods. Thus, as well as treating the inflammation seen in stroke patients, compositions comprising *Lactobacillus fermentum* ME-3 can also be used as adjuvant treatments for patients who have suffered a stroke.

The present invention therefore encompasses alleviating the symptoms of (particularly the inflammatory symptoms of) and/or providing adjuvant treatment for stroke.

Thus there are particularly important applications for *Lactobacillus fermentum* ME-3 as a prophylactic. Administration of *Lactobacillus fermentum* ME-3 may delay or prevent the onset of inflammatory diseases (preferably metabolic syndrome and/or metabolic syndrome related disorders). This is particularly relevant for subjects who are asymptomatic but who may be at risk of developing such diseases and disorders. Examples of such patient groups are defined above.

Compositions Comprising *Lactobacillus fermentum* ME-3

In the context of the present invention, *Lactobacillus fermentum* ME-3 can be administered in any suitable formulation such as a food product, a food supplement or a pharmaceutical composition. Formulations for probiotic compositions are disclosed in WO 2010/069920, WO 2002/005829, EP 1 699 474

Suitable food products include a medical food or functional food product. In one embodiment the food product, medical food or functional food is a dairy product such as milk, yogurt, cheese, kefir, or a milk-based or a whey-based fermented dairy product. Chocolate based products, as described in Example 5 are also suitable as food products containing and administering *Lactobacillus fermentum* ME-3.

Suitable pharmaceutical compositions that may be used in the invention include compositions comprising encapsulated *Lactobacillus fermentum* ME-3, for example in freeze-dried form, *Lactobacillus fermentum* ME-3 formulated in a coated or in a tablet or capsule form or *Lactobacillus fermentum* ME-3 formulated in a powder form. Suitable tablets and capsules include hard gelatin or vegetable capsules, tablets with or without enterocoating (e.g., those that dissolve in neutral conditions), and chewable tablets (Saxelin M, Clin Infect Dis. (2008) 46 (Supplement 2): S76-S79.)

In addition to *Lactobacillus fermentum* ME-3, the compositions may contain any acceptable carrier(s) and/or excipients. These include, but are not limited to carriers such as dietary fibers, carbohydrates and microcellulose, and pharmaceutically acceptable carriers, including liquids such as water, saline, glycerol and ethanol. Auxiliary substances, such as wetting or emulsifying agents, pH buffering substances, and the like, can also be present in compositions used in the present invention. A thorough discussion of suitable carriers is available in the literature and in Philip P. Gerbino. 2005. Remington: The Science and Practice in Pharmacy. 21st Ed. Philadelphia, Pa., Lippicott Williams & Wilkins, ISBN: 0-7817-4673-6

The *Lactobacillus fermentum* ME-3 may be administered prior to, simultaneously with, or subsequently to another active compound, for example as an adjuvant treatment. Such active compounds include a further probiotic, a prebiotic, one or more vitamins, monocalin K, medicaments typically used to treat an inflammatory disease, for example a CVD, a neurodegenerative disease, Alzheimer's disease, atherosclerosis, cancer, stroke, a metabolic disorder, metabolic syndrome, prediabetes or type 2 diabetes and/or further anti-inflammatory agent(s). The other active compound may also be a statin. Examples of further probiotics include strains, e.g. of *Pediococcus*, another *lactobacillus*, a *Bifidobacterium*.

Medicaments used to treat inflammatory disorders include, but are not limited to: thrombolytics such as aspirin and tissue plasminogen activator (TPA); agents used to treat type 2 diabetes such as metformin, sitagliptin, saxagliptin, repaglinide, nateglinide, exenatide and liraglutide; agents used to treat atherosclerosis such as beta-blockers, ACE inhibitors, calcium channel blockers, statins and fibrates; and agents used to treat Alzheimer's disease such as cholinesterase inhibitors and NMDA receptor antagonists like donepezil hydrochloride, rivastigmine, galantamine and memantine.

Suitable anti-inflammatory agents include, but are not limited to: corticosteroids and non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen), aspirin and aspirin derivatives, and COX inhibitors.

The composition comprising *Lactobacillus fermentum* ME-3 may further comprise one or more vitamins and/or monocalin K. In particular, the composition comprising *Lactobacillus fermentum* ME-3 used in the present invention may further comprise or be administered prior to, simultaneously with, or subsequently to the composition described above and in EFSA Journal 2011; 9(7):2304.

An effective dose of *Lactobacillus fermentum* ME-3 in the context of the present invention is from about $10^6$ to about $10^{11}$ CFU per day, for example about $10^6$ to about $10^{10}$ CFU per day, preferably about $6 \times 10^9$ CFU. This dose can be administered as a single daily dose, or as a number of divided doses. For example, the dose may be administered as 2-6 divided doses, e.g 2-6, 2-4, 3-4 doses per day or 2, 3, 4, 5 or 6 doses per day. An individual dosage form may contain from about $10^6$ to about $10^{10}$ CFU, for example about $10^7$-$10^9$ CFU, preferably about $3 \times 10^9$ CFU. In one particular dosage form, a kefir comprises about $2 \times 10^8$ CFU/g and is administered at about 100-2000 ml per day, for example, about 100-1000, about 200-600 ml or about 300-400 ml per day. In a further specific dosage form, an individual capsule contains about $3 \times 10^9$ CFU or about $10^9$ CFU of freeze-dried *Lactobacillus fermentum* ME-3 and 1-10, e.g. 2-8, 3-6, 4-5, or 2, 3, 4, 5, or 6 capsules may be administered per day. Other components may be present. For example a preferred daily dose (2 capsules) comprises:

| Ingredient | Amount |
| --- | --- |
| Red rice yeast | 666 mg (10 mg monacolin K) |
| *Lactobacillus fermentum* ME-3 | 60 mg (6 billion CFU) |
| Ubiquinol (Kaneka QH ™) | 30 mg |
| L-Cystein | 30 mg |
| Vitamin E | 10 mg (85% of suggested daily dose) |
| Vitamin B1 | 0.66 mg (60% of suggested daily dose) |
| Vitamin B6 | 1 mg (72% of suggested daily dose) |
| Vitamin B9 | 100 µg (50% of suggested daily dose) |
| Vitamin B12 | 1.5 µg (60% of suggested daily dose) |

This is commercially available as REG'ACTIV® Cholesterol (www.regactiv.com/en/produits/product-1).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x+10%.

The term "subject" refers to an asymptomatic or clinically healthy individual.

The term "patient" refers to a symptomatic individual.

The term "adjuvant treatment" or "adjuvant component" in the context of the invention means that the composition comprising *Lactobacillus fermentum* ME-3 is used in conjunction with other medicaments and treatments for the same disorder, for example an inflammatory disorder and preferably a metabolic syndrome related disorder. The term includes the use of *Lactobacillus fermentum* ME-3 as a further adjuvant medicament component in conjunction with ordinary and routine treatments and medicaments for the inflammatory condition. The composition comprising *Lactobacillus fermentum* ME-3 can be used alone or as an "adjuvant treatment" or "adjuvant component" in any of the methods and uses specified herein.

EXAMPLES

Example 1

Figure 1:
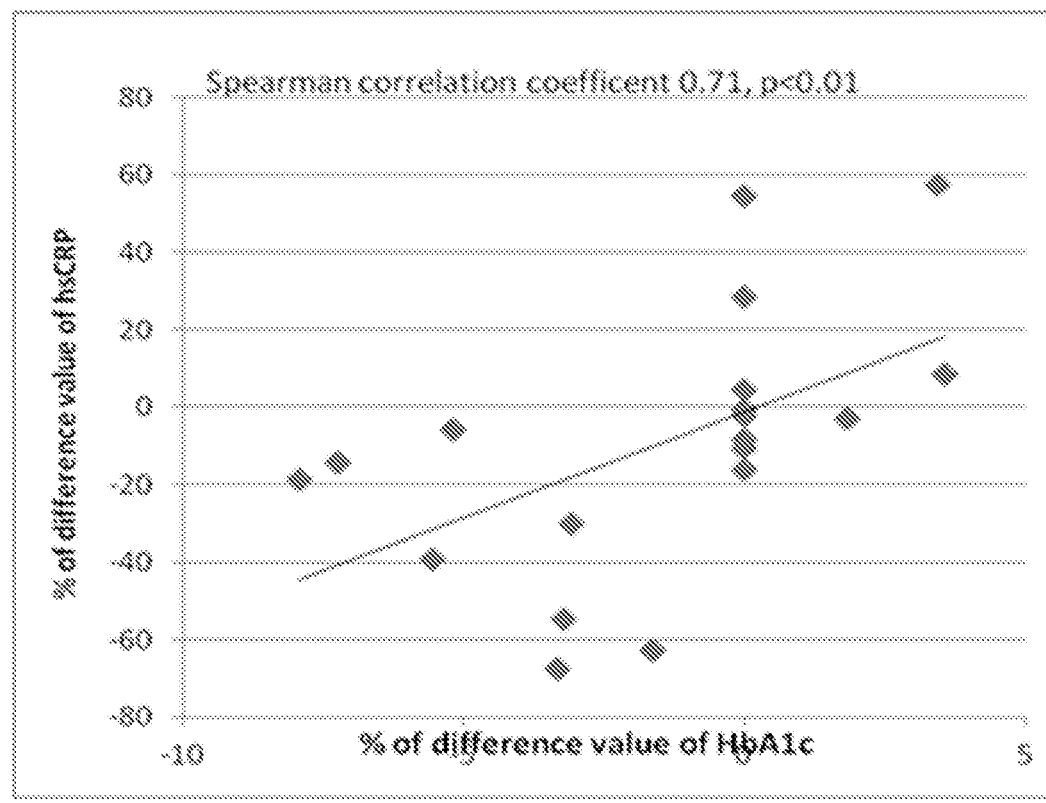
FIG. 1. The scatter plot on the relationship of values of high sensitive C-reactive protein (hsCRP) and glycated haemoglobin (HbA1c)—R=0.71, p<0.01, between baseline and endpoint values.

Effect of probiotic *Lactobacillus fermentum* ME-3 on low-grade inflammation markers hsCRP, HBA1c, IL-6, adiponectin and non-specific glycation markers was monitored.

Twenty three clinically healthy volunteers (16 females, 7 males, age 40-65 years) were recruited into a clinical open-label study. Exclusion criteria were as follows: an ongoing acute infection; diabetes; history of food allergy or gastrointestinal disease; use of any antimicrobial agent within the preceding month or use of any regular concomitant medication including non-steroidal anti-inflammatory drugs, statins or hormonal contraception; pregnancy or breastfeeding; alcohol abuse; use of drugs; special diets; smoking. During the intervention, and for two weeks beforehand, participants were asked to avoid vitamin or mineral supplementation, changes in accustomed diet habits and everyday physical activity, and use of probiotic-based foods or other kefirs/yogurts. Unfortunately, because of personal reasons, 4 participants (all men) did not finish the trial.

All participants signed their written informed consent and had the option of withdrawing from the study at any time. The Ethics Review Committee (ERC) on Human Research of the University of Tartu approved the study protocol (protocol No. 211/T-1). This study was carried out in accordance with the Declaration of Helsinki of the World Medical Association.

The kefir containing the probiotic *Lactobacillus fermentum* ME-3 was produced by AS Tere (Tallinn, Estonia). The viable count of *Lactobacillus fermentum* ME-3 in the kefir was stable in all purchased lots (viable counts $2 \times 10^8$ CFU/g kefir). The gelatine coated probiotic capsules used in Example 2 contained $10^9$ CFU of *Lactobacillus fermentum* ME-3 per capsule in addition to 250 mg of saccharose and microcellulose.

After two weeks introductory period (wash-out), baseline standard fasting blood (from the antecubital vein) were obtained. Samples were kept at $-80°$ C. until analyzed. Then participants received 200 ml of kefir containing the probiotic *Lactobacillus fermentum* ME-3 ($2 \times 10^9$ CFU/g kefir) daily for four weeks. After that standard fasting blood (from the antecubital vein) was obtained. Routine blood indices were assayed: glycated haemoglobin (HbA1c) using a certified Hitachi 912 automated analyzer in the local clinical laboratory (Roche Diagnostics LDL-Chol and HDL-Chol). The hsCRP was determined by a latex particle-enhanced immunoturbidimetric assay (Roche Diagnostics GmPh, Germany) with the automated analyzer Hitachi 912 [1]. Plasma level of IL-6 was measured by an ELISA using a commercially available kit (Human IL-6 Immunoassay, catalogue number D6050, R&D Systems Inc.®, Minneapolis, USA) and plasma level of adiponectin was measured by an ELISA using a commercially available kit (Human Total Adiponectin/Acrp30, catalogue number DRP300, SRO300 PDRP300, R&D Systems Inc.®, Minneapolis, USA).

The level of inflammatory markers hsCRP and IL-6 decreased after 4 weeks of consumption of kefir containing the probiotic *Lactobacillus fermentum* ME-3, as well as the level HbA1c. Over the same period, the adiponectin levels increased. Thus, the consumption of probiotic *Lactobacillus fermentum* ME-3 alleviates the risk of inflammatory diseases like cardiovascular and neurodegenerative diseases, atherosclerosis, metabolic disorders, metabolic syndrome related conditions (prediabetes, diabetes, cardiovascular disease) and type 2 diabetes.

Statistics

Calculations were performed using commercially available statistical software packages (Statistics for Windows, Stat Soft Inc. and Graph Pad PRISM Version 2.0) and software R, version 1.6.0 for Windows (www.r-project.org). All values are given as mean and standard deviation (mean±SD). Statistically significant differences between the groups were determined by using Student's t-test. In all analyses, P values<0.05 were considered to be statistically significant. Correlations between the variables were examined using linear regression analysis (software R, version 2.0.1 for Windows).

TABLE 1

Inflammatory and non-specific glycation markers at week 0 and after consumption of probiotic *Lactobacillus fermentum* ME-3 enriched kefir 200 g/per day for 4 weeks.

| | Healthy volunteers n = 19 | |
| --- | --- | --- |
| | Week 0 | Week 4 |
| hsCRP mg/L | 3.14 ± 2.68 | 2.11 ± 1.56 |
| | | p < 0.04 |
| IL-6 pg/ml | 2.73 ± 1.31 | 2.46 ± 1.06 |
| | | p < 0.02 |
| HbA1c % | 5.96 ± 0.33 | 5.86 ± 0.27 |
| | | p < 0.03 |
| Adiponectin (ng/ml) | 8.62 ± 3.94 | 9.10 ± 3.85 |
| | | p < 0.03 | hsCRP decreased as well as HbA1c and had statistically significant correlation between each other in 0 week, 1=0.48, p=0.037 as well as in 4 week r-0.54, p=0.018 (the Spearman correlation coefficient).

Responsiveness of the subjects was very good. In the case of hsCRP it is 58%, in the case of IL-10—68%, HbA1c responsiveness is 26% and adiponectin is more than 70%.

The consumption of probiotic *Lactobacillus fermentum* ME-3 statistically significantly lowered the level of hsCRP as well as the level of IL-6. At the same time the long-term blood sugar (as HbA1c) level decreased being in good correlation in with lowered values of hsCRP (R=0.71, p<0.01).

This very clearly shows the vicious cycle between the high-normal (low-level) inflammation on the cellular level and high-normal values of HbA1c. This strong correlation between inflammatory markers (hsCRP and IL-6) and non-specific glycation markers (HbA1c), when one of them increases for any reason the other will also increase. People, especially elderly, having either increased inflammation on cellular level or advanced-glycation, may have therefore have an increased risk of developing type 2 diabetes, cardiovascular and neurodegeneretive diseases. Additionally, persons having either increased inflammation on cellular level or a non-physiological level of glycation, have an increased risk for metabolic syndrome related conditions (prediabetes, diabetes, cardiovascular disease).

It follows that *Lactobacillus fermentum* ME-3 enriched food products, food supplement or compositions comprising *Lactobacillus fermentum* ME-3 can be used for alleviating and preventing low-grade (high-normal) inflammation on the cellular level because the levels of inflammatory markers hsCRP and IL-6 are decreased and anti-inflammatory marker adiponectin levels are increased after consumption such a food product, food supplement or composition.

It also follows that *Lactobacillus fermentum* ME-3 enriched food product, food supplement or medicine can be used for alleviating and preventing the elevated level of long term blood sugar by decreasing the level of glycated haemoglobin-HbA1c on cellular level.

It further follows that *Lactobacillus fermentum* ME-3 enriched food products, food supplements or compositions comprising *Lactobacillus fermentum* ME-3 can be used for alleviating and preventing and treating metabolic syndrome related conditions (prediabetes, diabetes, cardiovascular disease).

Example 2

21 patients (80.4±9.9 years, 9 men/12 women) who had 8-22 (12±6.6) days earlier brain stroke. The subjects of randomized, double-blind clinical study were randomly distributed into 2 groups and were assigned to consume twice a day either 3 capsules (per capsule 109 CFU) of freeze dried Lf ME-3 (LfME-3 group, 10 subjects or 3 capsules (containing 250 mg saccharose and microcellulose, control group, 11 subjects) for 3 weeks. The functional ability (Functional Independence Measure—FIM and Scandinavian Stroke Scale—SSS) and clinical indices of stroke patients were assessed pre- and after the 3 week treatment period. The use of usCRP for elevation of conditions thought to be associated with inflammation, in otherwise healthy individuals.

According to international reference values the accepted cut-off value for CRP is 20 mg/l (Van den Bruel A et al. (2011) BMJ. 2011 Jun. 8; 342). In the *Lactobacillus fermentum* ME-3 group 45% of stroke patients were above cut-off value for CRP prior to consuming *Lactobacillus fermentum* ME-3. After consumption, only 9% (one patient of 11) still had a CRP level above the cut off value.

Example 3

The Inventors also carried out a randomized, double blind placebo controlled clinical trial (The Ethics Review Committee (ERC) on Human Research of the University of Tartu approved the study protocol (ref: 210/T-3) to compare a placebo kefir group without ME-3 (more than 55 people) and an ME-3 kefir group (more than 55 people) (article in preparation). Data from 8 weeks versus data from 4 weeks showed that consumption of *Lactobacillus fermentum* ME-3 enriched kefir, not placebo kefiir, significantly decreased the level of HbA1c (p=0.015). In addition, at 8 weeks only ME-3 kefir decreased significantly the level of IL-6 (p<0.01), the ratio of TG/HDL-Chol (a marker for insulin resistance, p=0.02) as well as the level of OxLDL and increased significantly the level of adiponectin (p<0.003). Thus, these data together show that compositions comprising *Lactobacillus fermentum* ME-3 help to prevent risk, alleviate the symptoms and treat metabolic syndrome related conditions (prediabetes, diabetes, cardiovascular disease). Data from 8 weeks versus data from 4 weeks showed that consumption of *Lactobacillus fermentum* ME-3 enriched kefir, not the placebo kefir, significantly decreased the level of HbA1c (p=0.015).

Example 4

Twenty five asymptomatic volunteers (16 females and 9 males) were recruited into a clinical open-label study. Exclusion criteria were as follows: an ongoing acute infection; diabetes; history of food allergy or gastrointestinal disease; use of any antimicrobial agent within the preceding month or use of any regular concomitant medication including non-steroidal antiinflammatory and anti-diabetic drugs, statins or hormonal contraception; pregnancy or breastfeeding; alcohol abuse; use of drugs; special diet. During the intervention, and for two weeks beforehand, participants were asked to avoid vitamin or mineral supplementation, changes in accustomed diet habits and everyday physical activity, and use of probiotic-based foods or other kefirs/yogurts. All participants signed their informed consent and had the option of withdrawing from the study at any time. The Ethics Review Committee (ERC) on Human Research of the University of Tartu approved the study protocol (protocol 229/T-18). This study was carried out in accordance with the Declaration of Helsinki of the World Medical Association.

Capsules contained probiotic *Lactobacillus fermentum* ME-3 and the daily dose (2 capsules) is shown below.

A preferred daily dose (2 capsules) comprises:

| Ingredient | Amount |
| --- | --- |
| Red rice yeast | 666 mg (10 mg monacolin K) |
| *Lactabacillus fermentum* ME-3 | 60 mg (6 billion CPU) |
| Ubiquinol (Kaneka QH ™) | 30 mg |
| L-Cystein | 30 mg |
| Vitamin E | 10 mg (85% of suggested daily dose) |
| Vitamin B1 | 0.66 mg (60% of suggested daily dose) |
| Vitamin B6 | 1 mg (72% of suggested daily dose) |
| Vitamin B9 | 100 µg (50% of suggested daily dose) |
| Vitamin B12 | 1.5 µg (60% of suggested daily dose) |

This is commercially available as REG'ACTIV® Cholesterol (www.regactiv.com/en/produits/product-1).

After two weeks introductory period, baseline standard fasting blood samples (from the antecubital vein) were obtained. Samples were kept at −80° C. until analyzed. Then participants received 2 capsules/per day for 4 weeks. After that standard fasting blood was obtained. Routine blood indices were assayed: HbA1c using a certified Hitachi 912 automated analyzer in the local clinical laboratory (Roche Diagnostics LDL-Chol and HDL-Chol). hsCRP was determined by a latex particle-enhanced immunoturbidimetric assay (Roche Diagnostics GmPh, Germany) with an automated Hitachi 912 analyzer (Pihl et al., 2003). Plasma levels of IL-6 were measured by ELISA using a commercially available kit (Human IL-6 Immunoassay, catalogue number D6050, R&D Systems Inc.®, Minneapolis, USA; plasma levels of IL-10 were measured by ELISA using a commercially available kit (Human IL-10 Immunoassay, catalogue number D1000B, R&D Systems Inc.®, Minneapolis, USA) and plasma levels of adiponectin were measured by an ELISA using a commercially available kit (Human Total Adiponectin/Acrp30, catalogue number DRP300, SRO300 PDRP300, R&D Systems Inc.®, Minneapolis, USA).

Statistics

Calculations were performed using commercially available statistical software packages (Statistics for Windows, Stat Soft Inc. and Graph Pad PRISM Version 2.0) and software R, version 1.6.0 for Windows (www.r-project.org). All values are given as mean and standard deviation (mean±SD). Statistically significant differences between the groups were determined by using Student's t-test. In all analyses, P values<0.05 were considered to be statistically significant. Correlations between the variables were examined using linear regression analysis (software R, version 2.0.1 for Windows).

TABLE 2

Markers and insulin intolerance/sensitivity signal (TG/HDL-Chl) at 0 weeks and after consumption of probiotic *Lactobacillus fermentum* ME-3 containing capsules, 2 capsules/per day, 4 weeks (an open label clinical trial).

| | Clinically healthy subjects, n = 25 | |
|---|---|---|
| | 0 weeks | 4 weeks |
| Cholesterol (mmol/L) | 6.6 ± 1.0 | 5.7 ± 0.8 p < 0.0001 |
| LDL-Chol (mmol/L) | 4.5 ± 0.9 | 3.6 ± 0.8 p < 0.00001 |
| HDL-Chol (mmol/L) | 1.66 ± 0.33 | 1.70 ± 0.35 |
| TG (mmol/L) | 1.5 ± 0.4 | 1.3 ± 0.3 p < 0.03 |
| TG/HDL-Chol | 1.0 ± 0.4 | 0.8 ± 0.3 p < 0.03 |
| hs CRP (mg/L) | 2.31 ± 1.44 | 1.88 ± 0.95 p = 0.035 |
| HbA1c % | 5.68 ± 0.21 | 5.51 ± 0.20 p = 0.043 |
| oxLDL U/L | 80.58 ± 16.69 | 65.77 ± 12.6 p < 0.0003 |
| IL-6 (pg/ml) | 2.2 ± 0.6 | 1.9 ± 0.5 p < 0.05 |
| IL-10 (pg/ml) | 6.4 ± 2.0 | 7.3 ± 2.6 p = 0.034 |

The level of LDL-Chol as well as total cholesterol and oxLDL decreased significantly 95% of all participants and HDL-Chol increase showed tendency to increase after 4 weeks consumption of *Lactobacillus fermentum* ME-3 capsules. The level of inflammatory markers hsCRP and IL-6 decreased after 4 weeks consumption *Lactobacillus fermentum* ME-3 capsules as well as the level of glycated Hb (HbA1c) and the level of anti-inflammatory interleukin IL-10 increased. The responsiveness in the case of hsCRP and IL-10 was about 60%, for IL-6 it was about 70% and for HbA1c it was about 60%.

Insulin resistance is associated with autonomic dysfunction. An attenuated decrease in heart rate after exercise (or heart rate recovery [HRR]) predicts all-cause mortality and is believed to reflect decreased parasympathetic activity. Utilizing the triglyceride/HDL-Chol ratio as a marker of insulin resistance (a prediabetes, diabetes related marker) we found that after consumption of capsules the TG/HDL-Chol ratio decreased significantly and showed responsiveness of about 76%. Thus, data from Examples 3 and 4 together show that compositions comprising *Lactobacillus fermentum* ME-3 help to prevent risk, alleviate the symptoms and treat metabolic syndrome related conditions (prediabetes, diabetes, cardiovascular disease).

Example 5

*Lactobacillus fermentum* ME-3 chocolate-based compositions

The stability of freeze dried *Lactobacillus fermentum* ME-3 in chocolate at 42 C during 3 weeks was investigated. The materials used were freeze dried *Lactobacillus fermentum* ME-3 $10^8$ CFU/g (produced by Probiotical SpA, Novara, Italy) and commercially available chocolates with different cacao concentration. 50 grams of chocolate consisting respectively of 85%, 70%, 56% and 30% cacao were melted on hot water and maintained at 42° C. using a thermostat. Evaluation of CFU-s were made at time point 0, and at the first, second and third weeks. The chocolate samples were weighed and the respective amount of PBS buffer with a ratio of 1:9 was added. Dilutions at $10^1$-$10^8$ were made and plated out with deMan, Rogosa and Sharpe (MRS) medium.

Figure 2:
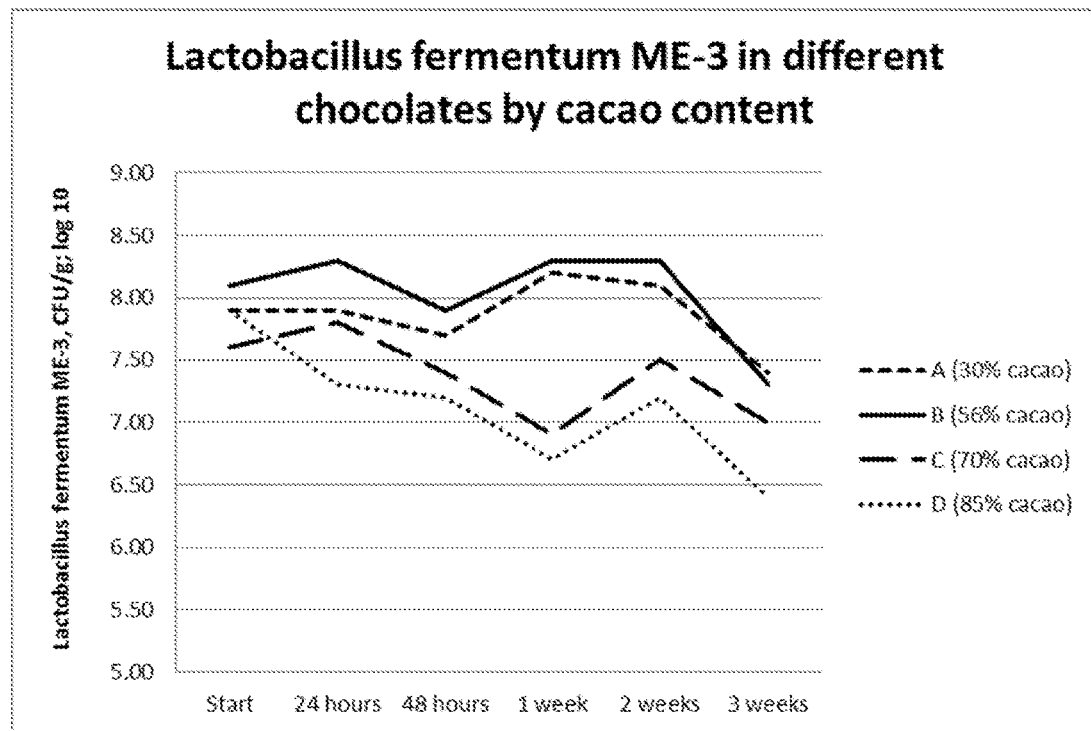
FIG. 2. *Lactobacillus fermentum* ME-3 in different chocolates, CFU/g.

Survival within 3 weeks was confirmed. Loss of cell count remained mainly under 1 log (in chocolate A: 7.4-8.2; B: 7.3-8.3; C: 6.9-7.8; D: 6.4-7.9), except chocolate D with 85% of cacao (see FIG. 2).

The invention claimed is:

1. A method of delaying the onset of or treating, alone or as an adjuvant component, a metabolic syndrome related disorder selected from prediabetes, cardiovascular disease and type 2 diabetes in a subject who is asymptomatic for said metabolic syndrome related disorder and who has a CRP level of 3-10 mg/L, comprising administering an effective amount of a composition comprising *Lactobacillus fermentum* ME-3 strain DSM 14241 to said subject.

2. A method of delaying the onset of, or treating, alone or as an adjuvant component, a metabolic syndrome related disorder selected from prediabetes, cardiovascular disease and type 2 diabetes in a subject who is asymptomatic for said metabolic syndrome related disorder and who has a CRP level of 3-10 mg/L by simultaneously:
  a. decreasing the level of glycated haemoglobin HbA1c;
  b. decreasing or preventing low-grade inflammation on a cellular level; and
  c. increasing the level of adiponectin,
comprising administering an effective amount of a composition comprising *Lactobacillus fermentum* ME-3 strain DSM 14241 to said subject.

3. The method of claim 2, wherein the inflammation on a cellular level is measured using the pro-inflammatory markers high sensitive C-reactive protein (hsCRP) and interleukin-6(IL-6).

4. The method of claim 1, wherein said composition is a food product, a food supplement or a pharmaceutical composition.

5. The method of claim 4, wherein the food product is a medical food product or a functional food product.

6. The method of claim 4, wherein the food product is a dairy product such as milk, yogurt, cheese, kefir, or a milk- or whey-based fermented dairy product, or a chocolate product.

7. The method of claim 1, wherein said composition is administered prior to, simultaneously with, or subsequently to another active compound.

8. The method of claim 1, wherein said composition further comprises one or more vitamins and/or monacolin K.

9. The method of claim 1, wherein said composition comprises *Lactobacillus fermentum* ME-3 strain DSM 14241 in an encapsulated form, in a freeze-dried form, in a coated form, in a capsule, in a tablet or in a powder.

10. The method of claim 1, wherein $10^6$-$10^{11}$ colony forming units (CFU-s) of said *Lactobacillus fermentum* ME-3 strain DSM 14241 are administrated daily.

11. The method of claim 7, wherein said active compound is an anti-inflammatory composition, one or more vitamins, and/or monacolin K.

* * * * *